US012108170B2

(12) United States Patent
Culman et al.

(10) Patent No.: US 12,108,170 B2
(45) Date of Patent: Oct. 1, 2024

(54) MULTIPLE BAND PASS BAYER PATTERN FILTER

(71) Applicant: INTUITIVE SURGICAL OPERATIONS, INC., Sunnyvale, CA (US)

(72) Inventors: William Jason Culman, Sunnyvale, CA (US); Jeffrey M. DiCarlo, Austin, TX (US); Ian E. McDowall, Woodside, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 926 days.

(21) Appl. No.: 17/259,834

(22) PCT Filed: Jul. 1, 2019

(86) PCT No.: PCT/US2019/040178
§ 371 (c)(1),
(2) Date: Jan. 12, 2021

(87) PCT Pub. No.: WO2020/014031
PCT Pub. Date: Jan. 16, 2020

(65) Prior Publication Data
US 2021/0307687 A1 Oct. 7, 2021

(51) Int. Cl.
| | |
|---|---|
| *H04N 25/131* | (2023.01) |
| *A61B 1/00* | (2006.01) |
| *A61B 5/00* | (2006.01) |
| *A61B 34/00* | (2016.01) |
| *A61B 90/30* | (2016.01) |
| *G02B 5/20* | (2006.01) |
| *A61B 34/35* | (2016.01) |

(52) U.S. Cl.
CPC ....... *H04N 25/131* (2023.01); *A61B 1/00009* (2013.01); *A61B 5/0077* (2013.01);
(Continued)

(58) Field of Classification Search
None
See application file for complete search history.

(56) References Cited

U.S. PATENT DOCUMENTS

| | | | |
|---|---|---|---|
| 4,974,076 A | 11/1990 | Nakamura et al. | |
| 5,255,087 A * | 10/1993 | Nakamura ............ | G01J 3/0235 348/E5.038 |

(Continued)

FOREIGN PATENT DOCUMENTS

| | | |
|---|---|---|
| JP | 2009039510 A | 2/2009 |
| JP | 2015053979 A | 3/2015 |

(Continued)

OTHER PUBLICATIONS

International Preliminary Report on Patentability for Application No. PCT/2019/040178, mailed on Jan. 21, 2021, 16 pages.

(Continued)

*Primary Examiner* — James M Hannett

(57) ABSTRACT

An image sensing apparatus including a pixel array comprising two or more photo-sensor elements, a first optical filter disposed on a first photo-sensor element of the pixel array and a second optical filter disposed on a second photo-sensor element of the pixel array. The first optical filter is configured such that a spectral response of the first optical filter includes a first passband in a first wavelength range and a second passband in a second wavelength range, where the first passband and the second passband are separated by a first stop band. The second optical filter is configured such that a spectral response of the second optical filter includes a third passband in the first wavelength range and a fourth passband in the second wavelength range, where the third passband and the fourth passband are separated by a second stop band.

20 Claims, 11 Drawing Sheets

(52) U.S. Cl.
CPC ............ *A61B 5/4887* (2013.01); *A61B 5/742* (2013.01); *A61B 34/25* (2016.02); *A61B 90/30* (2016.02); *G02B 5/201* (2013.01); *A61B 34/35* (2016.02)

(56) References Cited

U.S. PATENT DOCUMENTS

| | | | |
|---|---|---|---|
| 2004/0006275 | A1 | 1/2004 | Demos et al. |
| 2009/0021739 | A1* | 1/2009 | Tsujita ................. H04N 25/134 356/407 |
| 2013/0300837 | A1* | 11/2013 | DiCarlo ............... A61B 1/0646 348/46 |

FOREIGN PATENT DOCUMENTS

| | | |
|---|---|---|
| WO | WO-2004005868 A2 | 1/2004 |
| WO | WO-2016100214 A1 | 6/2016 |

OTHER PUBLICATIONS

International Search Report and Written Opinion for Application No. PCT/US2019/040178, mailed Sep. 10, 2019, 18 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Bargigia I., et al., "Diffuse Optical Characterization of Collagen Absorption From 500 to 1700 nm," Journal of Biomedical Optics, Jan. 2017, vol. 22(1), pp. 1-7.
Extended European Search Report for Application No. EP23212771.2, mailed on Feb. 19, 2024, 15 pages.
Nachabé R., et al., "Diagnosis of Breast Cancer Using Diffuse Optical Spectroscopy From 500 to 1600 nm: Comparison of Classification Methods," Journal of Biomedical Optics, Aug. 2011, vol. 16(8), pp. 1-12.
Tsai C., et al., "Near-infrared Absorption Property of Biological Soft Tissue Constituents," Journal of Medical and Biological Engineering, Mar. 2001, vol. 21(1), pp. 7-14.

* cited by examiner

MULTIPLE BAND PASS BAYER PATTERN FILTER

PRIORITY CLAIM

This Application is a U.S. National Stage Application under U.S.C. § 371 and claims the benefit of International Patent Application No. PCT/US2019/040178, filed on Jul. 1, 2019, which claims priority to U.S. Provisional Application 62/697,102, filed on Jul. 12, 2018, the entire contents of both of which are incorporated herein by reference.

TECHNICAL FIELD

This disclosure relates to devices and methods for minimally invasive computer-assisted tele-operated surgery.

BACKGROUND

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. The surgeon performs the surgical procedures on the patient by manipulating master control input devices, which in turn control the motion of robotic instruments.

SUMMARY

In one aspect, this document features an image sensing apparatus that includes a pixel array comprising two or more photo-sensor elements, a first optical filter disposed on a first photo-sensor element of the pixel array and a second optical filter disposed on a second photo-sensor element of the pixel array. The first optical filter is configured such that a spectral response of the first optical filter includes a first passband in a first wavelength range, and a second passband in a second wavelength range, where the first passband and the second passband being separated by a first stop band. The second optical filter is configured such that a spectral response of the second optical filter includes a third passband in the first wavelength range, and a fourth passband in the second wavelength range, where the third passband and the fourth passband being separated by a second stop band. In some instances, a portion of the first stop band overlaps with a portion of the second stop band. In some instances, the first wavelength range is within the visible wavelength range, and the second wavelength range is outside the visible wavelength range. In some instances, the first and second wavelength ranges include 400-1700 nm. In some instances, the first wavelength range is 400-800 nm and the second wavelength range is about 800-1700 nm. This split allows for easy capture of a visible image. In some instances, for example, the wavelength ranges are trimodal, where the three wavelength ranges are, for example, 400-650 nm, 650-900 nm, and 900-1700 nm. In other instances, different wavelength ranges are possible in order to capture all of some portions of the visible and infrared wavelength spectrum (e.g., 400-1700 nm). In another aspect, this document features an image sensing apparatus that includes a pixel array comprising two or more photo-sensor elements, a first optical filter disposed on a first photo-sensor element of the pixel array, a second optical filter disposed on a second photo-sensor element of the pixel array, and a third optical filter disposed on a third photo-sensor element of the pixel array. The first optical filter is configured such that a spectral response of the first optical filter includes a first passband in a first wavelength range, and a second passband in a second wavelength range, where the first passband and the second passband being separated by a first stop band. The second optical filter is configured such that a spectral response of the second optical filter includes a third passband in the first wavelength range, and a fourth passband in the second wavelength range, where the third passband and the fourth passband being separated by a second stop band. In addition, the third optical filter is configured such that a spectral response of the third optical filter includes a fifth passband in the first wavelength range, and a sixth passband in the second wavelength range, and the fifth passband and the sixth passband are separated by a third stop band. In some instances, the first, second, and third optical filters are arranged in a Bayer pattern. In some instances, a portion of the first stop band overlaps with a portion of the second stop band and a portion of the third stop band.

In another aspect, this document features an image sensing apparatus that includes a pixel array comprising two or more photo-sensor elements, a first optical filter disposed on a first photo-sensor element of the pixel array and a second optical filter disposed on a second photo-sensor element of the pixel array. The first optical filter is configured such that a spectral response of the first optical filter includes a first passband in a first wavelength range, and a second passband in a second wavelength range, where the first passband and the second passband being separated by a first stop band. The second optical filter is configured such that a spectral response of the second optical filter includes a third passband in the first wavelength range, and a fourth passband in the second wavelength range, where the third passband and the fourth passband being separated by a second stop band. The image sensing apparatus features one or more processing devices configured to generate a representation of an image of using output signals from the pixel array, and circuitry configured to provide the output signals from the pixel array to the one or more processing devices. In some instances, the one or more processing devices are configured to generate the representation of the image by combining electromagnetic radiation received by the pixel array in the first wavelength range, and electromagnetic radiation received by the pixel array in the second wavelength range. In some instances, the one or more processing devices are configured to present the representation of the image on one or more displays.

In another aspect, this document features a surgical system that includes one or more display devices, an image sensing apparatus configured to receive electromagnetic radiation reflected or transmitted from a surgical scene, one or more processing devices, and an input device configured to receive a user-input for controlling at least a portion of a surgical device. The image sensing apparatus includes a pixel array comprising two or more photo-sensor elements, a first optical filter disposed on a first photo-sensor element of the pixel array and a second optical filter disposed on a second photo-sensor element of the pixel array. The first optical filter is configured such that a spectral response of the first optical filter includes a first passband in a first wavelength range and a second passband in a second wavelength range, and the first passband and the second passband are separated by a first stop band. The second optical filter is configured such that a spectral response of the second optical filter includes a third passband in the first wavelength range and a fourth passband in the second wavelength range, and the third passband and the fourth passband are separated by a second stop band. The one or more processing devices are configured to obtain a representation of a first image of a surgical scene using electromagnetic radiation in the first wavelength range, obtain a representation of a second image of the surgical scene using electromagnetic radiation in the second wavelength range, and present a visual representation of the surgical scene on the one or more displays. Where the visual representation is rendered using the representation of the first image and the representation of the second image and the user-input of the input device is received in response to presenting the visual representation.

In some instances, obtaining the representation of the first and second image, includes illuminating the surgical scene using electromagnetic radiation in a first illumination range and a second illumination range and obtaining the representations of the first image or second image responsive to illuminating the surgical scene using electromagnetic radiation in the first illumination range and second illumination range, respectively. In some instances, illuminating the surgical scene using electromagnetic radiation in the first wavelength range or the second wavelength range includes illuminating the surgical scene using electromagnetic radiation in the first illumination range during a first time period and illuminating the surgical scene using electromagnetic radiation in the second illumination range during a second time period that is at least partially non-overlapping with the first time period. In some instances, the representation of the second image is obtained at substantially the same time as the representation of the first image.

In another aspect, this document features method of providing visual feedback during a surgical process using a visual representation of a surgical scene rendered on one or more displays associated with a surgical device. The method includes illuminating a surgical scene using electromagnetic radiation in a first illumination-wavelength range, obtaining, responsive to illuminating the surgical scene using electromagnetic radiation in the first illumination-wavelength range, a representation of a first image of the surgical scene using a pixel array including two or more photo-sensor elements, illuminating the surgical scene using electromagnetic radiation in a second illumination-wavelength range, obtaining, responsive to illuminating the surgical scene using electromagnetic radiation in the second illumination-wavelength range, a representation of a second image of the surgical scene using the pixel array, and presenting the visual representation of the surgical scene on the one or more displays, wherein the visual representation is rendered using the representation of the first image and the representation of the second image. Where a first photo-sensor element of the two or more photo-sensor elements is configured to receive electromagnetic radiation though a first filter that includes a first passband in a first wavelength range and a second passband in a second wavelength range, the first passband and the second passband being separated by a first stop band, and where a second photo-sensor element of the two or more photo-sensor elements is configured to receive electromagnetic radiation though a second filter that includes a third passband in the first wavelength range and a fourth passband in the second wavelength range, the third passband and the fourth passband being separated by a second stop band.

In some instances, the first image corresponds to the electromagnetic radiation received through the first and third passbands and the second image corresponds to the electromagnetic radiation received through the second and fourth passbands. In some instances, illuminating the surgical scene using electromagnetic radiation in the first illumination-wavelength range comprises illuminating the surgical scene during a first time period; and wherein illuminating the surgical scene using electromagnetic radiation in the second illumination-wavelength range comprises illuminating the surgical scene during a second time period that is at least partially non-overlapping with the first time period. In some instances, the first wavelength range of the first and third passbands lies inside the visible range, and where the second wavelength of the second and fourth passbands range lies outside the visible range. In some instances, the electromagnetic radiation in the first illumination-wavelength range lies inside the visible range, and wherein electromagnetic radiation in second first illumination-wavelength range lies outside the visible range.

In another aspect, this document features method of providing visual feedback during a surgical process using a visual representation of a surgical scene rendered on one or more displays associated with a surgical device. The method includes illuminating a surgical scene using electromagnetic radiation in a first illumination-wavelength range, obtaining, responsive to illuminating in the first illumination-wavelength range, a representation of a first image of the surgical scene using a pixel array including two or more photo-sensor elements, illuminating the surgical scene using electromagnetic radiation in a second illumination-wavelength range and obtaining, responsive to illuminating in the second illumination-wavelength range, a representation of a second image of the surgical scene using the pixel array, illuminating the surgical scene using electromagnetic radiation in a third illumination-wavelength range, and obtaining, responsive to illuminating in the third illumination-wavelength range, a representation of a third image of the surgical scene using the pixel array. Where a first photo-sensor element of the two or more photo-sensor elements is configured to receive electromagnetic radiation though a first filter that includes a first passband in a first wavelength range, a second passband in a second wavelength range, and a fifth passband in a third wavelength range the first passband and the second passband being separated by a first stop band, and where a second photo-sensor element of the two or more photo-sensor elements is configured to receive electromagnetic radiation though a second filter that includes a third passband in the first wavelength range, a fourth passband in the second wavelength range, and a sixth passband in the third wavelength range. The third passband and the fourth passband are separated by a second stop band and the first and second filters together define a third stop band separating the fifth and sixth passbands from the first, second, third, and fourth passbands. The method includes presenting the visual representation of the surgical scene on the one or more displays, wherein the visual representation is rendered using the representation of the first image, the representation of the second image, and the representation of the third image.

Implementations of the above aspects can include one or more of the following.

An input device can be used to receive user-input for controlling at least a portion of the surgical device, wherein the user-input is received in response to presenting the visual representation. In some implementations, the user-input enables a toggling between the visual representation and a normal surgical view. The first tissue type can be collagen, and the second tissue type can be lipid. The visual representation can include enhanced visible differences between a representation of a ureter and a representation of surrounding lipid layers. In some instances, each of the first wavelength range and the second wavelength ranges are in the range 700-2000 nm. In other instances, the wavelength ranges capture only a portion of the infrared or visible spectrum. For example, a first wavelength range can be 1300-1350 nm and a second wavelength range can be 1200-1250 nm.

Obtaining the representation of the first or second image of the surgical scene using electromagnetic radiation of the first or second wavelength range, respectively, can include illuminating the surgical scene using electromagnetic radiation of the first wavelength range or the second wavelength range, and generating the representation of the first image or second image, respectively, using data captured by the one or more sensors, wherein the one or more sensors are configured to sense portions of the electromagnetic radiation reflected or transmitted from the surgical scene. Illuminating the surgical scene using electromagnetic radiation in the first wavelength range or the second wavelength range can include illuminating the surgical scene using electromagnetic radiation in the first wavelength range during a first time period, and illuminating the surgical scene using electromagnetic radiation in the second wavelength range during a second time period that is at least partially non-overlapping with the first time period. The representation of the first image can be generated in a wavelength range that lies inside the visible range of wavelengths. The representation of the second image can be generated in a wavelength range that lies outside the visible range of wavelengths, and the representations of the first and second images can be combined to generate the visual representation of the surgical scene.

A representation of a third image of the surgical scene can be obtained based on a third wavelength range that lies outside the visible range of wavelengths, and the visual representation of the surgical scene can be presented on the display, wherein the visual representation is rendered also using the representation of the third image. The third wavelength range can be selected such that an absorption of electromagnetic radiation in the third wavelength range for lipid is substantially equal to an absorption of electromagnetic radiation in the third wavelength range for collagen. The third wavelength range can be selected such that an absorption of electromagnetic radiation in the third wavelength for lipid is substantially different from an absorption of electromagnetic radiation in the third wavelength range for collagen.

Some or all of the embodiments described herein may provide one or more of the following advantages. Visible differences between two or more different types of tissues can be enhanced in images presented on a surgeon's display device. In some cases, where the different tissue types are adjacent to one another, this may assist the surgeon to access only the desired tissues, thereby potentially improving the accuracy of the surgical process. For example, by judicious selection of imaging wavelengths that enhance the differences between collagen and lipid, the technology described herein may allow for improved visualization of the urethra (which consists primarily of collagen) in the presence of surrounding layers of lipids. This in turn may assist some surgeons, in particular less experienced surgeons, to perform surgeries on a telesurgery system with increased confidence.

DETAILED DESCRIPTION

Figure 1B:
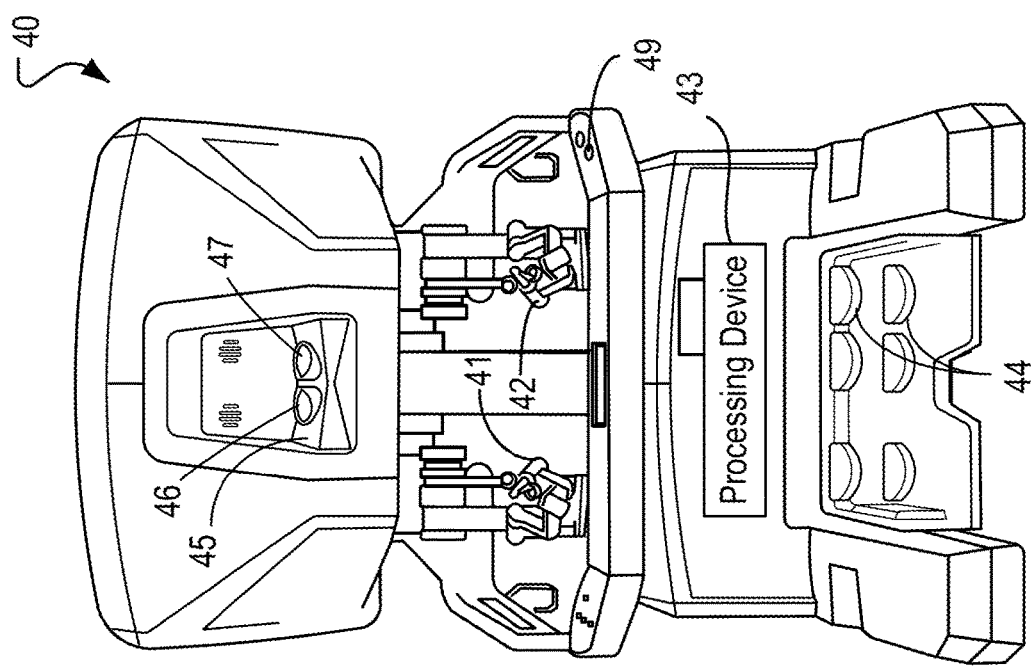
FIG. 1B is a front view of an example surgeon console of a computer-assisted tele-operated surgery system.

This document describes technology that allows for each pixel in an image sensing apparatus to capture information in multiple frequency ranges. For example, each pixel can include a front-end optical filter having multiple distinct passbands, such that separate channels of information may be captured by the same pixel upon illumination by electromagnetic radiation in corresponding frequency ranges. This in turn allows for implementation of a multi-spectral imaging apparatus without having to use additional pixels that would degrade the resolution of the apparatus. In some cases, the multi-spectral imaging can improve visualization of surgical sites and anatomical parts during image-guided surgical processes such as minimally invasive robotic surgery (also referred to herein as minimally invasive surgery (MIS)) without adversely affecting resolution of an underlying imaging apparatus. For example, the technology allows for enhancing visible differences between different tissue types at a surgical site, as displayed on a surgeon's console. In some cases, the high-resolution, multi-spectral imaging in turn may allow for improved visualization of tissues that may otherwise be relatively indistinguishable in the presence of adjacent tissues of a different kind. The technology described herein allows two or more different images to be generated using a same set of pixels in response to two different illumination wavelengths, where each of the two or more images represents distinct spectral response passbands of the pixels (or the front-end optical filters corresponding to the pixel). In some instances, the distinct spectral response passbands corresponding to the optical filters for the different pixels are grouped into two or more distinct wavelength ranges such that information capture under illumination in one wavelength range does not substantially affect information capture under illumination in the other wavelength range(s). In some cases, the passbands of the optical filters can be configured (and the corresponding illumination ranges may be selected) to enhance visible differences between tissues being imaged.

Aspects of the technology are described primarily in terms of an implementation using a da Vinci® Surgical System, commercialized by Intuitive Surgical, Inc. of Sunnyvale, California. Examples of such surgical systems are the da Vinci® Xi™ Surgical System (Model IS4000) and the da Vinci® Si™ HD™ Surgical System (Model IS3000). It should be understood that aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are described for illustrative purposes, and are not to be considered as limiting the scope of the inventive aspects disclosed herein. As applicable, inventive aspects may be embodied and implemented in both relatively smaller, hand-held, hand-operated devices and relatively larger systems that have additional mechanical support, as well as in other embodiments of computer-assisted tele-operated medical devices.

Figure 1A:
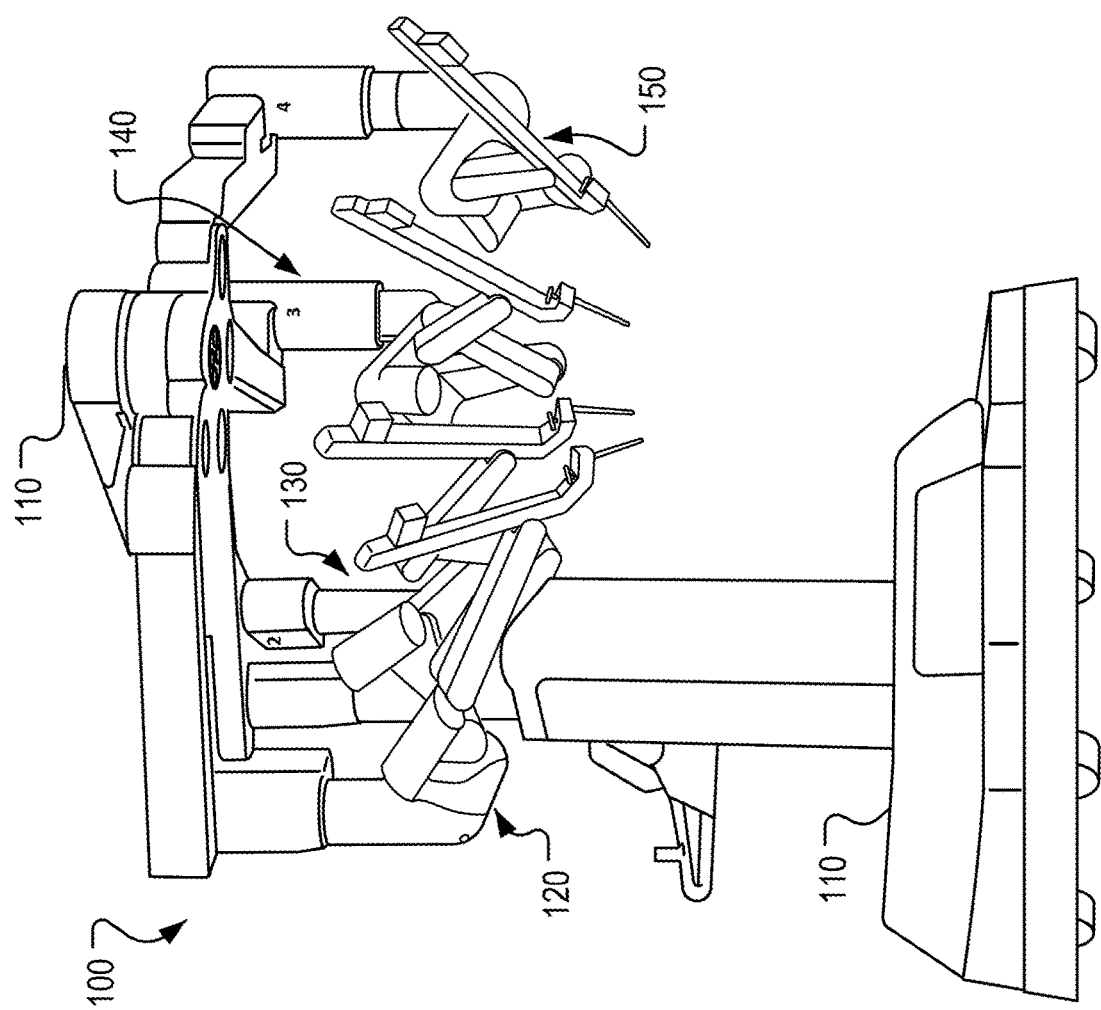
FIG. 1A is a perspective view of an example patient-side cart of a computer-assisted tele-operated surgery system.

Referring to FIGS. 1A and 1B, systems for minimally invasive computer-assisted telesurgery (also referred to as MIS) can include a patient-side cart 100 and a surgeon console 40. Telesurgery is a general term for surgical systems where the surgeon uses some form of remote control, e.g., a servomechanism, or the like, to manipulate surgical instrument movements rather than directly holding and moving the instruments by hand. The robotically manipulatable surgical instruments can be inserted through small, minimally invasive surgical apertures to treat tissues at surgical sites within the patient, avoiding the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side cart 100 includes a base 110, a first robotic manipulator arm assembly 120, a second robotic manipulator arm assembly 130, a third robotic manipulator arm assembly 140, and a fourth robotic manipulator arm assembly 150. Each robotic manipulator arm assembly 120, 130, 140, and 150 is pivotably coupled to the base 110. In some embodiments, fewer than four or more than four robotic manipulator arm assemblies may be included as part of the patient-side cart 100. While in the depicted embodiment, the base 110 includes casters to allow ease of mobility, in some embodiments the patient-side cart 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that another instrument may be introduced at the surgical site. Alternatively, the remaining robotic manipulator arm assembly may be used for introducing a second endoscope or another image-capturing device, such as an ultrasound probe, to the surgical site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device so that it may be pivoted about the pivot point, inserted into and retracted out of the entry aperture, and rotated about its shaft axis.

In the depicted embodiment, the surgeon console 40 includes a stereo vision display 45 so that the user may view the surgical work site in stereo vision from images captured by the stereoscopic camera of the patient-side cart 100. Left and right eyepieces, 46 and 47, are provided in the stereo vision display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices 49, which in turn control the motion of robotic instruments.

The surgeon console 40 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six degrees-of-freedom ("DOF"). Foot pedals 44 with toe and heel controls are provided on the surgeon console 40 so the user may control movement and/or actuation of devices associated with the foot pedals.

A processing device 43 is provided in the surgeon console 40 for control and other purposes. The processing device 43 performs various functions in the medical robotic system. One function performed by processing device 43 is to translate and transfer the mechanical motion of input devices 41, 42 to actuate their respective joints in their associated robotic manipulator arm assemblies 120, 130, 140, and 150 so that the surgeon can effectively manipulate devices, such as the surgical instruments. Another function of the processing device 43 is to implement the methods, cross-coupling control logic, and controllers described herein.

The processing device 43 can include one or more processors, digital signal processors (DSPs), and/or microcontrollers, and may be implemented as a combination of hardware, software and/or firmware. Also, its functions as described herein may be performed by one unit or divided up among a number of subunits, each of which may be implemented in turn by any combination of hardware, software and firmware. Further, although being shown as part of or being physically adjacent to the surgeon console 40, the processing device 43 may also be distributed as subunits throughout the telesurgery system. One or more of the subunits may be physically remote (e.g., located on a remote server) to the telesurgery system.

Figure 1C:
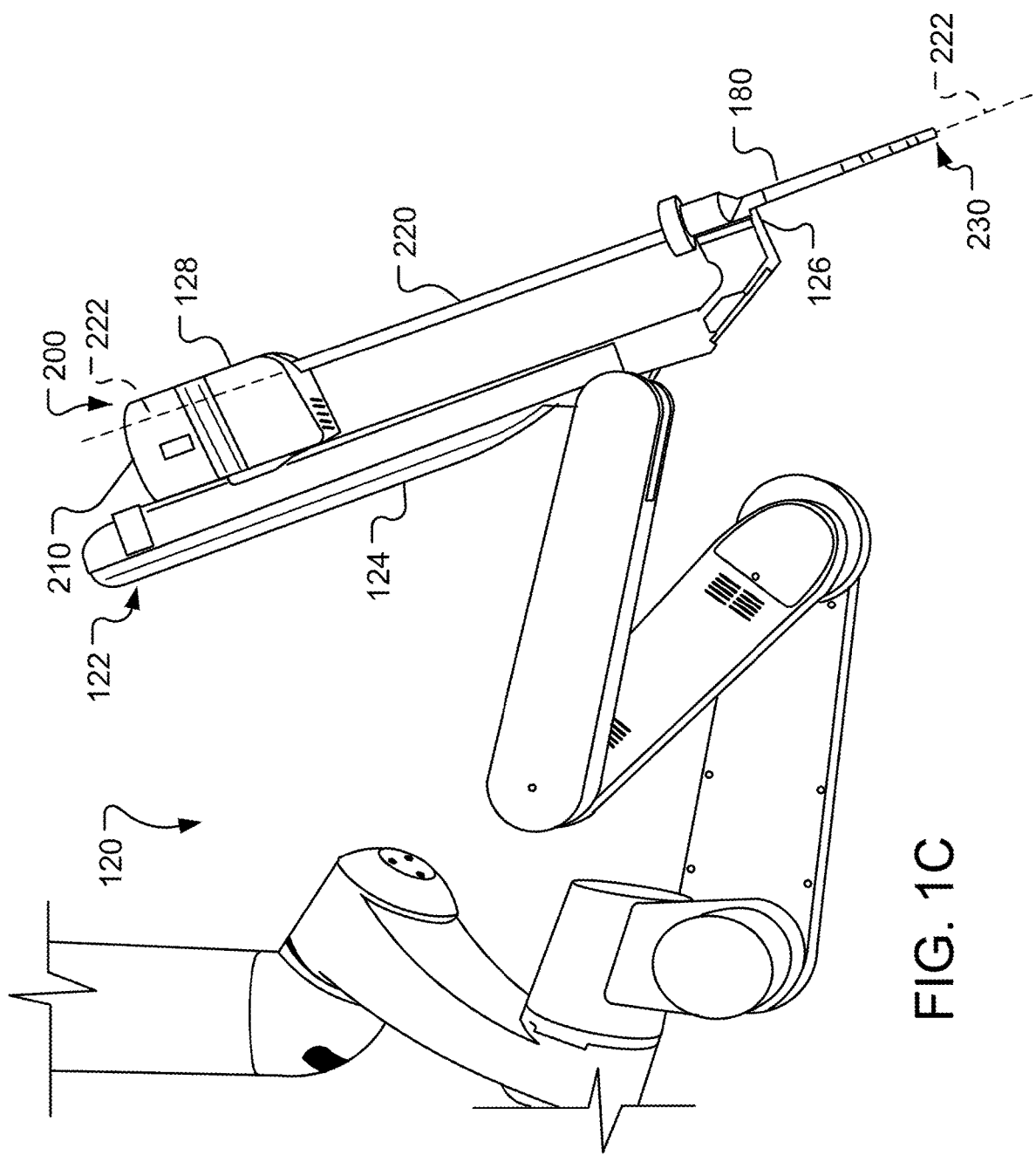
FIG. 1C is a side view of an example robotic manipulator arm assembly of a computer-assisted tele-operated surgery system.

Referring also to FIG. 1C, the robotic manipulator arm assemblies 120, 130, 140, and 150 can manipulate devices such as surgical instruments to perform MIS. For example, in the depicted arrangement the robotic manipulator arm assembly 120 is pivotably coupled to an instrument holder 122. A cannula 180 and a surgical instrument 200 and are, in turn, releasably coupled to the instrument holder 122. The cannula 180 is a tubular member that is located at the patient interface site during a surgery. The cannula 180 defines a lumen in which an elongate shaft 220 of the surgical instrument 200 is slidably disposed. As described further below, in some embodiments the cannula 180 includes a distal end portion with a body wall retractor member. The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable from the surgeon console 40 and processor 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processor 43. The surgical instrument 200 includes a transmission assembly 210, the elongate shaft 220, and an end effector 230. The transmission assembly 210 may be releasably coupled with the instrument holder carriage 128. The shaft 220 extends distally from the transmission assembly 210. The end effector 230 is disposed at a distal end of the shaft 220.

The shaft 220 defines a longitudinal axis 222 that is coincident with a longitudinal axis of the cannula 180. As the instrument holder carriage 128 translates along the instrument holder frame 124, the elongate shaft 220 of the surgical instrument 200 is moved along the longitudinal axis 222. In such a manner, the end effector 230 can be inserted and/or retracted from a surgical workspace within the body of a patient.

Figure 2:
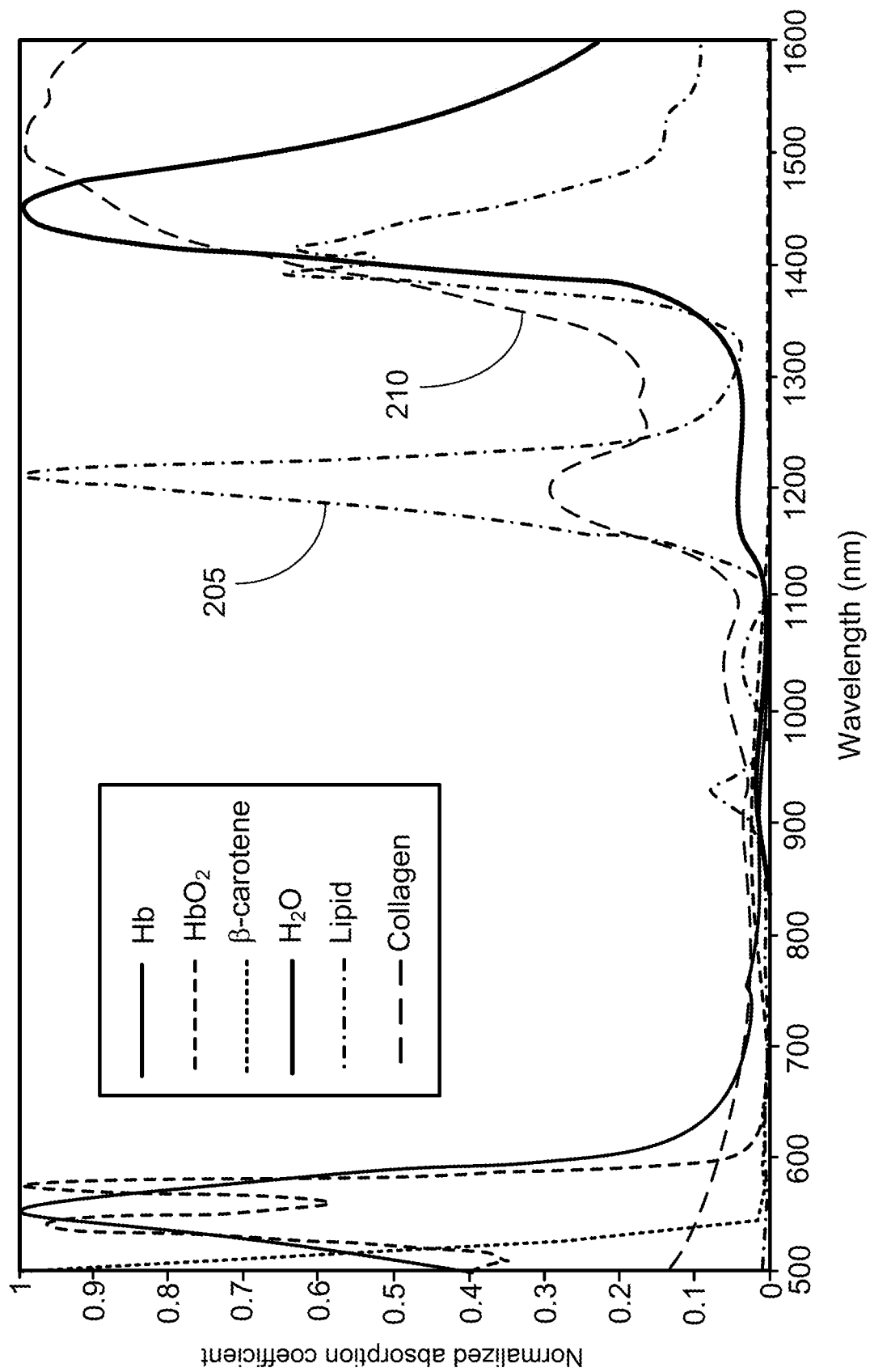
FIG. 2 is a collection of plots illustrating experimental results on absorption of electromagnetic radiation by different materials and tissues in a human body.

In some implementations, in order to enhance the visible differences between different tissues in the representations rendered on the surgeon's console 40, the illumination wavelengths wavelength ranges can be selected in accordance with the tissues being imaged. Light interacts with different tissues in different ways, for example, due to corresponding variations in absorption, reflection, and/or scattering of light. In some implementations, the illumination wavelengths or wavelength ranges can be selected, for example, based on experimental or theoretical knowledge about the absorption and/or reflection characteristics of the corresponding tissues being imaged. FIG. 2 is a collection of plots that illustrates experimental results on absorption of electromagnetic radiation by different materials and tissues in a human body. The x-axis of FIG. 2 represents wavelengths, and the y-axis represents normalized absorption coefficients. Therefore, FIG. 2 illustrates the variation in absorption characteristics of various components of a human body over the depicted range of wavelengths.

Figure 5A:
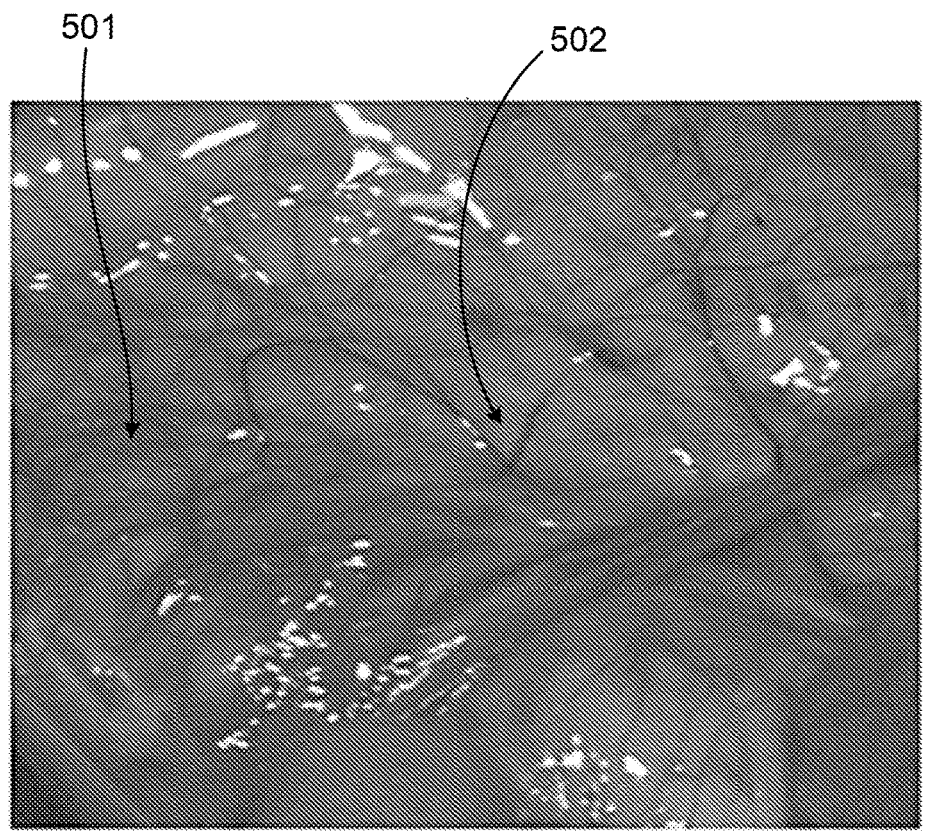
FIG. 5A shows a ureter in a human body in the presence of adjacent blood vessels, as captured in a first image obtained using illumination in a first illumination range.

From the experimental results depicted in FIG. 2, it can be observed that the absorption characteristics of some components are generally similar in the visible range or spectrum of wavelengths. For example, by comparing the plot 205 for lipid (fats) and the plot 210 for collagen (connective tissue), it can be observed that the normalized absorption coefficient for both remain generally low (around 0.1 or lower) at lower wavelengths until about 1100 nm. This range includes the upper end of about 700 nm of the visible spectrum. Therefore, imaging lipids and collagens using illumination in the visible spectrum results in similar absorption by the two types of tissues, which can sometimes make it challenging to distinguish them in the resulting image. An example of this is shown in FIG. 5A, which shows a ureter in a human body in the presence of adjacent and covering layers of fat, as captured in a typical broadband image obtained using wavelengths in the visible spectrum. The portion 501 represents the location of the ureter in the image, and the portion 502 represents the surrounding tissue. However, because the characteristics in the visible spectrum are substantially similar for lipids and collagens, the boundary between the ureter and the surrounding tissue may be quite subtle and hard to see.

Figure 3A:
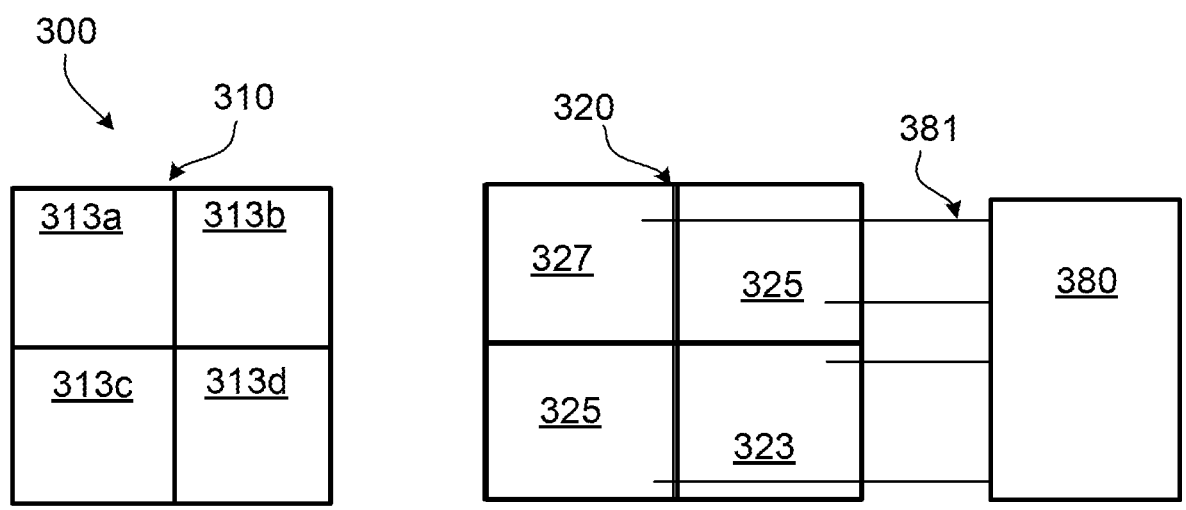
FIG. 3A shows an illustration of an image sensing apparatus.

FIG. 3A is an illustration of an image sensing apparatus 300 that includes an array 310 of optical filters, an array 320 of pixels underlying the array of filters 310, and one or more processing devices 380 configured to process the information captured by the array 320 of pixels. The array 320 includes multiple photo-sensor elements 323a, 323b, 323c, and 323d (323, in general, also referred to as pixels) that are configured to produce electrical signals in response to electromagnetic radiation incident on the pixels. The one or more processing devices 380 are in electrical communication 381 with each of the photo-sensor elements 323 and are configured to produce one or more images based on the received electrical signals. The filter array 310 is positioned adjacent and above the array 320, with individual optical filters 313a, 313b, 313c, and 313d (313, in general) arranged to filter the electromagnetic radiation incident on the corresponding photo-sensor elements 323. In traditional Bayer pattern filter arrays, the filters 313a and 313d are configured to pass wavelengths in the "red" and "blue" portions of the spectrum, and the filters 313b and 313c are configured to pass wavelengths in the "green' portion of the spectrum. Such filters however are not configured to capture information in more than one channel under separate illumination ranges.

Figure 4A:
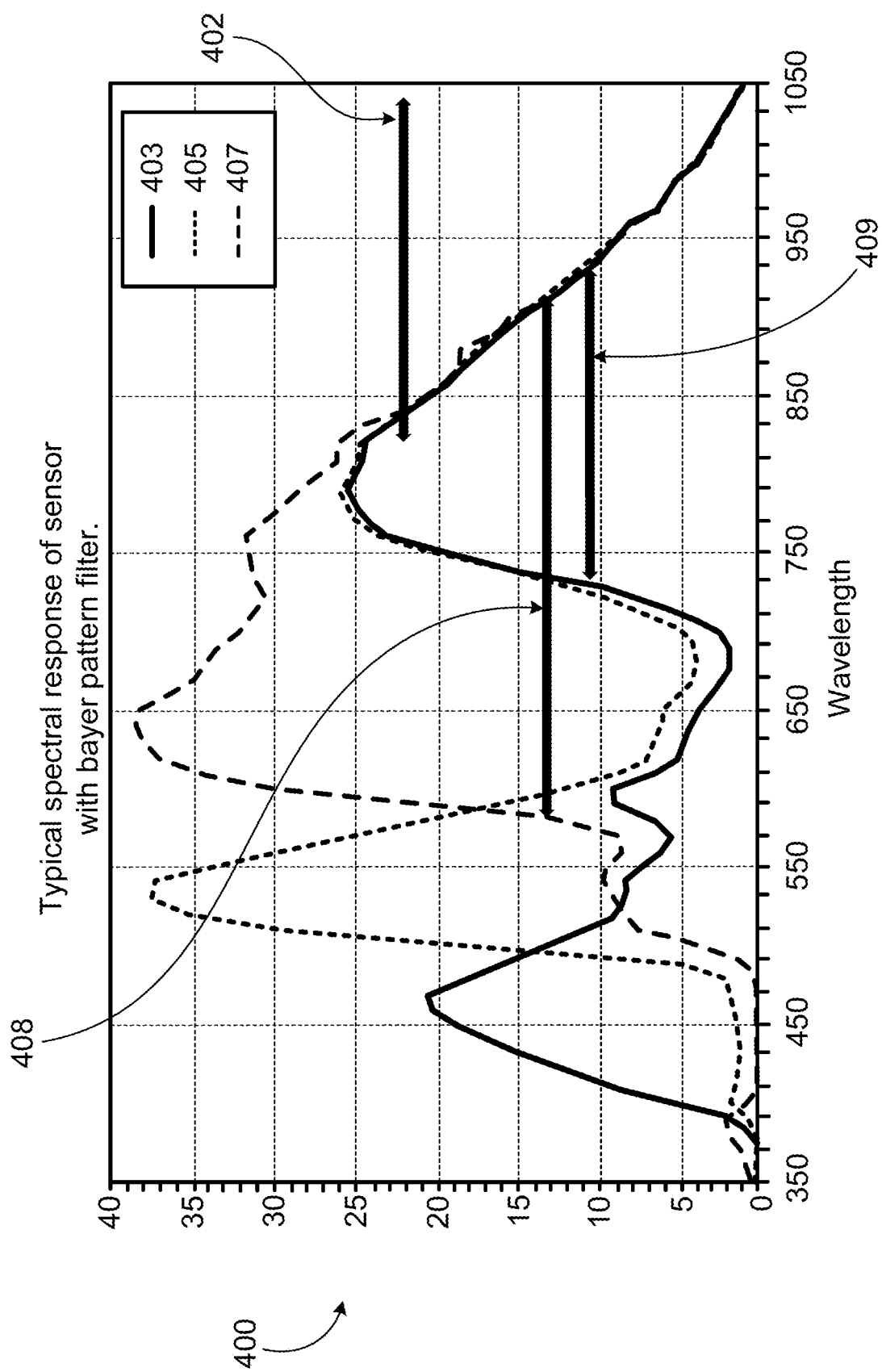
FIG. 4A shows the spectral response of a typical imaging sensor with a Bayer pattern filter.

FIG. 4A shows example spectral responses 400 of optical filters in an array that includes three filters arranged in a typical Bayer pattern, where the spectral response 403, 405, 407 of the filters are configured to differentiate colors in the visible spectrum (e.g., 350 nm to 700 nm). FIG. 4A shows first and second filter responses 403, 405 each defining a bimodal shape, with a third filter response 407 that does not. In addition, the passbands 409 of the first and second filter responses 403, 405 overlap with each other and the passband 408 of the third filter response 407. Moreover, the spectral response of all three filter responses 403, 405, 407 are identical in a wavelength range 402 the near infrared (e.g., about 800 nm to 1050 nm). Due to this identical spectral response, near infrared electromagnetic radiation cannot be color-differentiated by a prior art sensor having the characteristics illustrated in FIG. 4A.

Figure 4B:
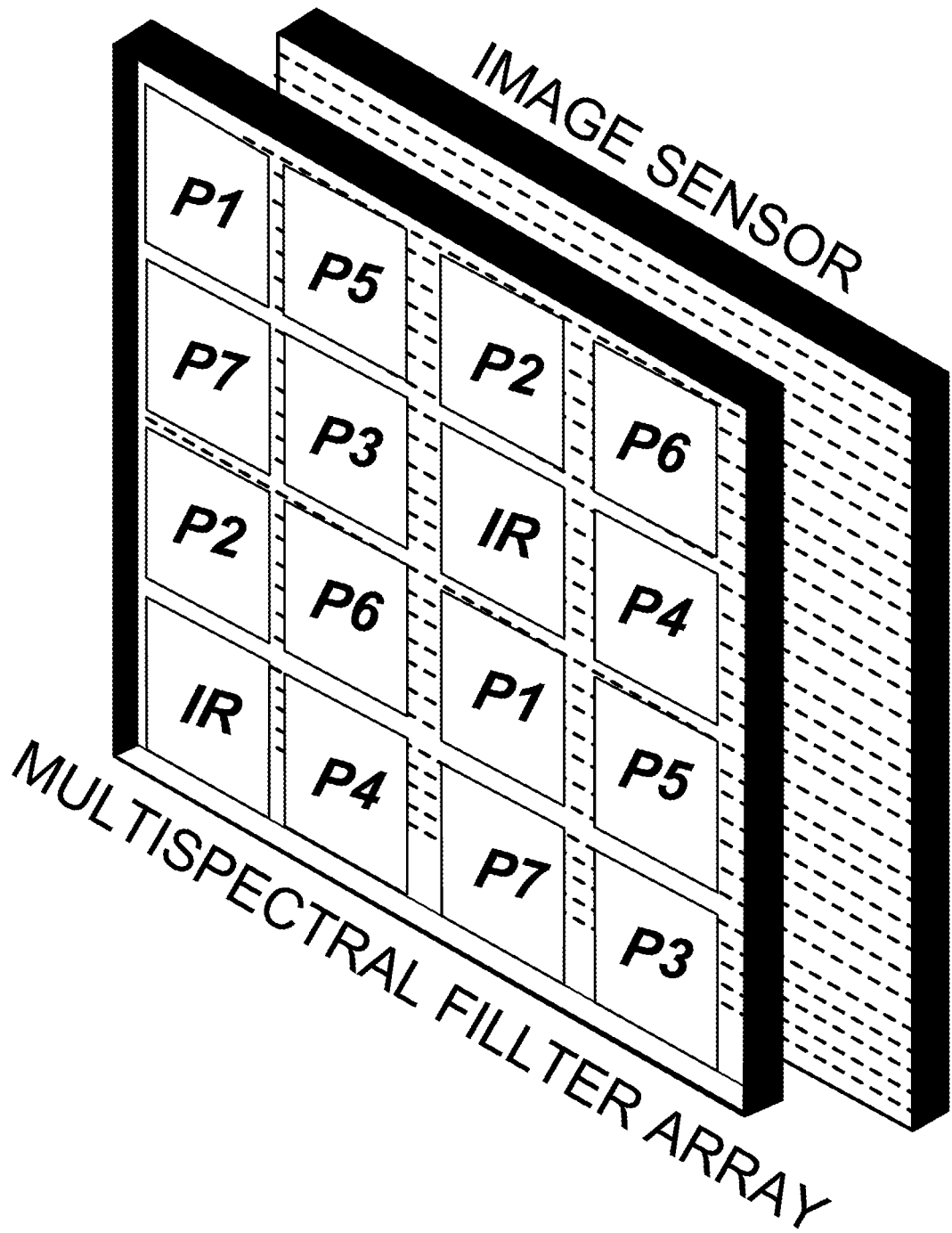
FIG. 4B shows a prior art image multi-spectral sensing apparatus.
Figure 4C:
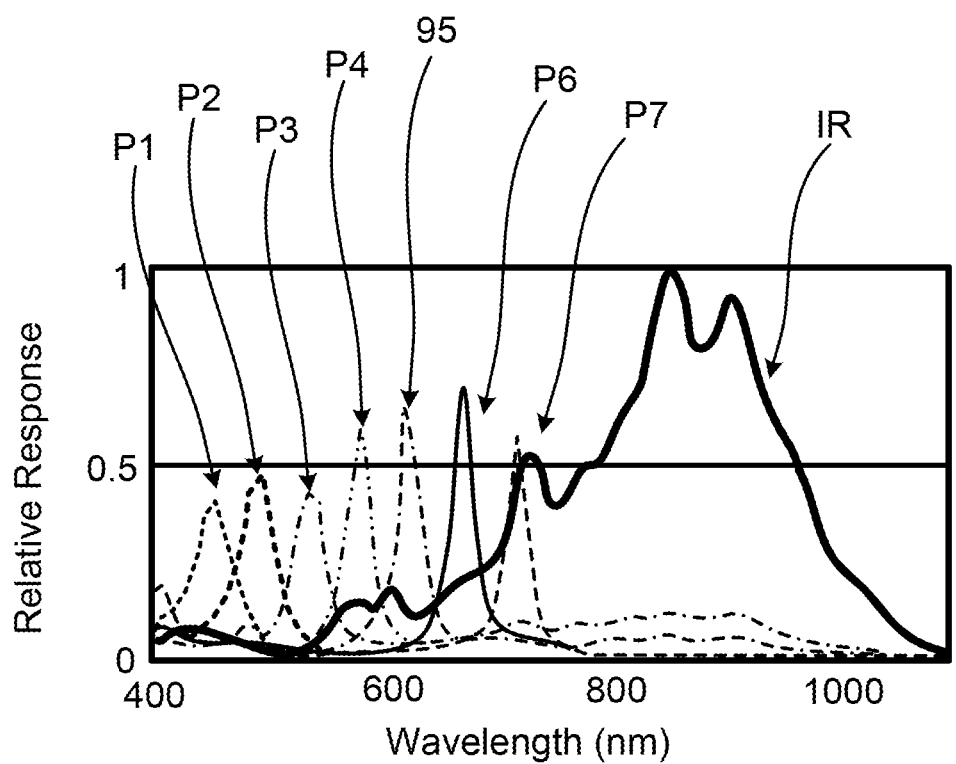
FIG. 4C shows the spectral response of the prior art image multi-spectral sensing apparatus of FIG. 4B.

Because optical filters used in typical Bayer pattern arrays do not have multiple passbands that can be separately grouped into distinct wavelength ranges, such optical filters are not directly used for multi-spectral imaging. Rather, traditional multi-spectral imaging approaches use additional optical filters configured to pass wavelengths in corresponding additional wavelength ranges. An example of such a filter array is shown in FIG. 4B, where an optical filter array 410 is positioned above an image sensor 420 includes an array of pixels. The optical filter array 410 includes a plurality of individual filters (P1-P7) each defining a different passband the visible spectrum, and an infrared filter (IR) defining a dedicated passband in the infrared spectrum. FIG. 4C shows the spectral response of the image sensor of FIG. 4B, where the spectral response of each filter (P1-P7) includes a narrow passband range in the visible spectrum, and the spectral response of the infrared filter (IR) includes a very wide passband range in the infrared spectrum. The direct result of the large filter array 410 pattern of the sensor of FIG. 4B is a reduction in resolution compared to the typical Bayer pattern sensor of FIG. 4A.

The use of additional filters (as shown in FIG. 4B) correspondingly requires the use of additional image sensing elements or pixels. Therefore, for a given amount of available real estate, implementing a multi-spectral imaging system using the optical array of FIG. 4B degrades the resolution of the imaging system, as compared to a four-pixel Bayer pattern sensor. In contrast, the technology described herein allows for configuring the optical filters such that (i) each filter has multiple passbands with intervening stopbands, and (ii) the passbands for different optical filters in the array can be grouped together in multiple imaging wavelength ranges such that each such imaging wavelength range includes no more than a single passband of one optical filter. During the imaging process, if the illumination wavelength ranges are constrained such that the reflected/refracted/transmitted wavelengths coming from the imaging target are constrained within two or more of the individual imaging wavelength ranges, two or more corresponding images may be obtained using the same set of pixels. For example, the target can first be illuminated using a first illumination wavelength range such that the resulting light from the target is constrained within a first imaging wavelength range that includes one passband each of the different pixels. The captured information can thus be processed to generate a first image of the target. The target can then be illuminated using a different, second, illumination wavelength range such that the resulting light from the target is constrained within a second imaging wavelength range that includes a separate set of one passband each of the different pixels. The information captured under illumination by the second illumination range can be processed to generate a second image of the target. The first image and the second image can then be used to generate a multi-spectral image of the target.

Figure 3B:
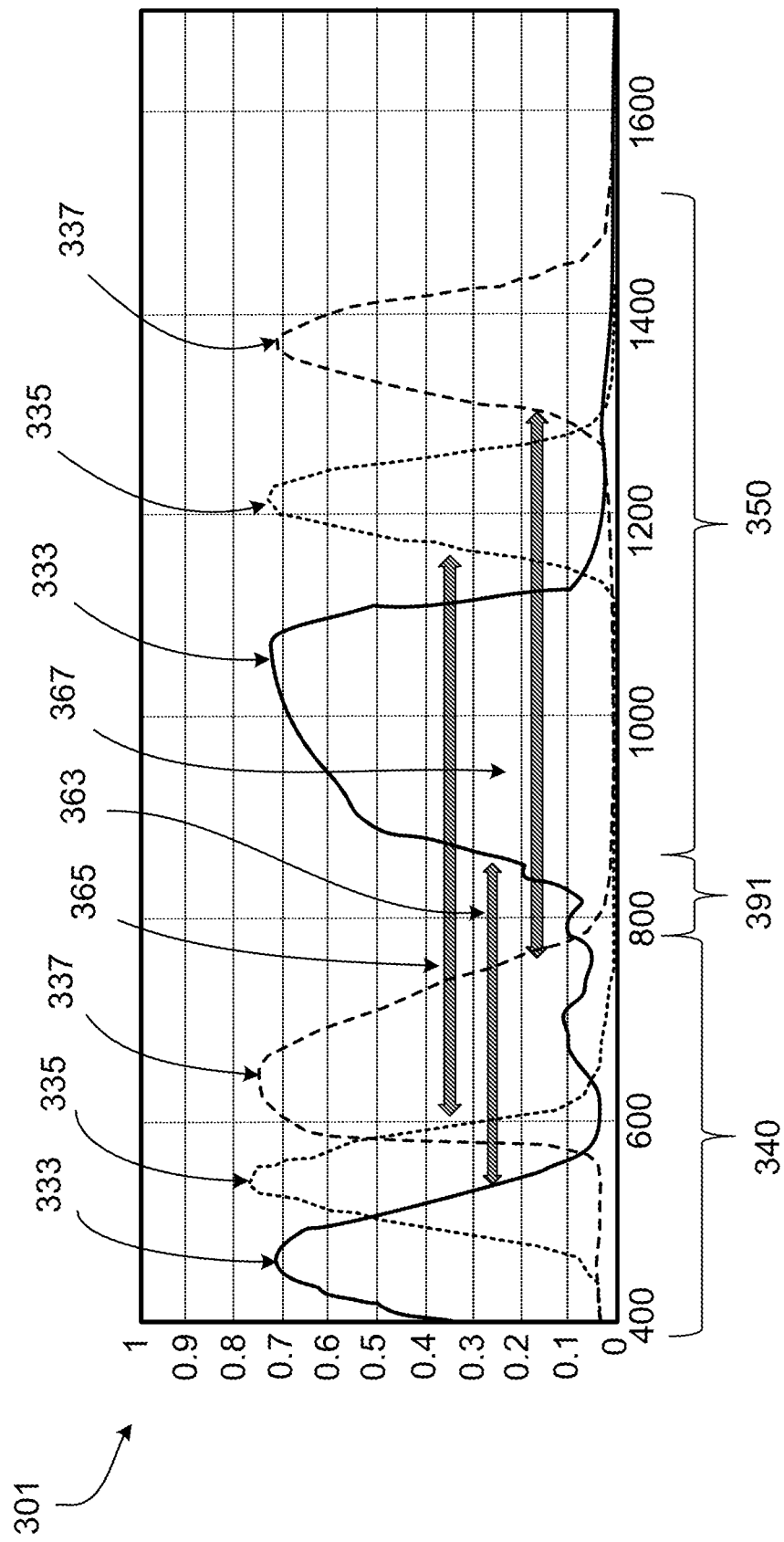
FIG. 3B shows the spectral response of the image sensing apparatus of FIG. 3A.

Referring now to FIG. 3B, and as discussed in more detail below, each optical filter 313 has at least two passbands in different wavelength ranges, and the passbands of each filter 313 are separated by a stop band. Therefore, each optical filter 313 allows electromagnetic radiation to be received by the corresponding photo-sensor element 323 in two distinct wavelength ranges. Further, the passbands of the different optical filters are configured such that a first set of passbands corresponding to the different optical filters are delimited within a first wavelength range that is non-overlapping with a second set of passbands corresponding to the different optical filters delimited with a second wavelength range.

For example, FIG. 3B shows a graph 301 the spectral response 333, 335, 337 of the image sensing apparatus 300 of FIG. 3A. A first filter 313a of the filter array 310 is arranged to filter electromagnetic radiation prior to being received by a first photo-sensing element 323a of the array 320. The first filter 313a defines a first spectral response 333 that forms a first passband in a first wavelength range 340 and a second passband in a second wavelength range 350, as illustrated by the bimodal shape of the first spectral response 333. The bimodal shape of the first spectral response 333 is defined by a first stop band 363 that separates the first passband from the second passband. The first stop band 363 represents frequencies of electromagnetic radiation that are much more strongly filtered by the first filter 313a than the frequencies of the two passbands (e.g., the two peaks of the first spectral response 333).

Similarly, a second filter 313a of the filter array 310 is arranged with respect to a second photo-sensing element 325 of the array 320. The second filter 313b, 313c defines a second spectral response 335 that forms a first passband in the first wavelength range 340 and a second passband in the second wavelength range 350, as illustrated by the bimodal shape of the second spectral response 335. The bimodal shape of the second spectral response 335 is defined by a second stop band 365 that separates the first passband from the second passband. The second stop band 365 represents frequencies of electromagnetic radiation that are much more strongly filtered by the second filter 313b, 313c than the frequencies of the two passbands (e.g., the two peaks in the second spectral response 335). Finally, a third filter 313d of the filter array 320 is arranged with respect to a third photo-sensing element 327 of the array 320. The third filter 313d defines a third spectral response 337 that forms a first passband in the first wavelength range 340 and a second passband in the second wavelength range 350, as illustrated by the bimodal shape of the third spectral response 337. The bimodal shape of the third spectral response 337 is defined by a third stop band 367 that separates the first passband from the second passband. The third stop band 367 represents frequencies of electromagnetic radiation that are much more strongly filtered by the third filter 313d than the frequencies of the two passbands (e.g., the two peaks in the third spectral response 337). In some instances, the stop bands 363, 365, 367 of the filter array 310 define an overlapping region 391 between the first frequency range 340 and the second frequency range 350.

In operation, the image sensing apparatus 300 is arranged to receive light from a surgical scene and the array 320 transmits a signal to the processor 380 that reflects to the spectral response of the filter array 310. However, because the spectral responses 333, 335, 337 of the filters 313a, 313b, 313c, 313d are bimodal, two different images can be generated using the image sensing apparatus 300 by exposing the surgical scene to illumination primarily in the first wavelength range 340 and generating a first image, and then illuminating the surgical scene to illumination primarily in the second wavelength range 350 and generating a second image. In this manner, a single filter 310 and array 320 are able to be construct two different color images using two different illuminations. In some instances, to generate the color images, the filters 313, 313b, 313c, 313d of the filter array 310 are arranged in a Bayer pattern. In some instances, the first wavelength range 340 includes all or a portion of the visible wavelength range (e.g., 390 nm to 700 nm) and the second wavelength range 350 includes infrared wavelengths outside of the visible spectrum (e.g., 900 nm to 1500 nm, as illustrated in FIG. 3B). As a result, the image sensing apparatus 300 is capable of capturing multi-spectral images without the resolution-degrading effects associated with adding additional pixels and filters (e.g., the sensor of FIG. 4A) to capture the additional spectral ranges. In some instances, capturing multi-spectral images by, making each of the filters bimodal or multimodal, in and of itself, may not generate the full array of advantages, and, in some aspects (and discussed in more detail below with respect to FIG. 4D), the passbands of the filters are configured such that each group of passbands are delimited within a wavelength range that is non-overlapping with another wavelength range that includes another group of passbands.

Referring again to FIG. 3B, because the image sensing apparatus 300 is configured to receive electromagnetic radiation from the surgical scene, and therefore the illumination wavelength range need not be the same as the wavelength ranges 340, 350 of the filter array 310, as the wavelength range of the electromagnetic radiation received by the image sensing apparatus also depends on the properties of the substances/tissues in the surgical scene which interact with the electromagnetic radiation illuminating the surgical scene before being sensed by the image sensing apparatus 300. In some instances, a first image, which may substantially represent the electromagnetic radiation in the first wavelength range (e.g., depending on the first illumination wavelength range and the properties of the surgical scene), is a true color image of the surgical scene and the second image, which may substantially represent the electromagnetic radiation in the second wavelength range, is a false color image of the surgical scene.

The imaging process using a selected set of wavelengths or wavelength ranges, as described above, may be implemented using various types of imaging systems. In some implementations, the image sensing apparatus 300 is a camera sensor that includes a pixel array formed with a charge-coupled device (CCD), a complementary metal oxide semiconductor (CMOS) detectors, or the like, where each photo-sensing element 323, 325, 327 is responsive to a wavelength range that encompasses the first and second wavelength ranges 340, 350 in order to enable the array 320 to detect both passbands of the filters 313, 313b, 313c, 313d. In some instances, and as described in more detail below with respect to FIG. 4D, the filters 313, 313b, 313c, 313d may each include three or more passbands, where the passbands are separated by stop bands and the three or more passbands are grouped into three or more corresponding wavelength ranges in order to enable three or more corresponding images to be generated in response to illumination in three or more corresponding illumination wavelength ranges.

The filter array 310 may also be referred to as a multi-bandwidth filter 310 due to the nature of having two or more distinct response regions (e.g., the first and second wavelength ranges 340, 350), which can produce images in each of the wavelength ranges 340, 350 and enables the individual images to be combined into one multi-bandwidth representation that can be manipulated to provide a singular view of a surgical scene, but with specific frequency ranges (e.g., from one of the images) being highlighted in order to improve the visibility or detection or certain tissues types of structures. In operation, the surgical site may be illuminated using different spectrums, each having illumination wavelengths that corresponds to the different sensitivity bands of the filter array 310 that causes the target tissues to reflect or transmit at the selected wavelengths or wavelength ranges of the filter array 310. The reflected or transmitted electromagnetic radiation from the tissues can then be sequentially collected by the image sensing apparatus 300 in order to create the distinct images, which can then be further processed into one multi-bandwidth image.

In operation, the image sensing apparatus may be used for obtaining representations of multiple bandwidth-limited images. For example, the surgical site may be sequentially illuminated using different narrow wavelengths (e.g., corresponding to one or more of the passbands) and the same image sensing apparatus 300 can be used to capture the electromagnetic radiation transmitted or reflected from the target tissues. The illumination wavelengths can be selected in accordance with the selected wavelengths for the target tissue types, as described above. Such narrowband illumination can be achieved, for example, using laser sources. Other implementations, including those that use a combination of the above-mentioned techniques, are also within the scope of this disclosure.

Figure 4D:
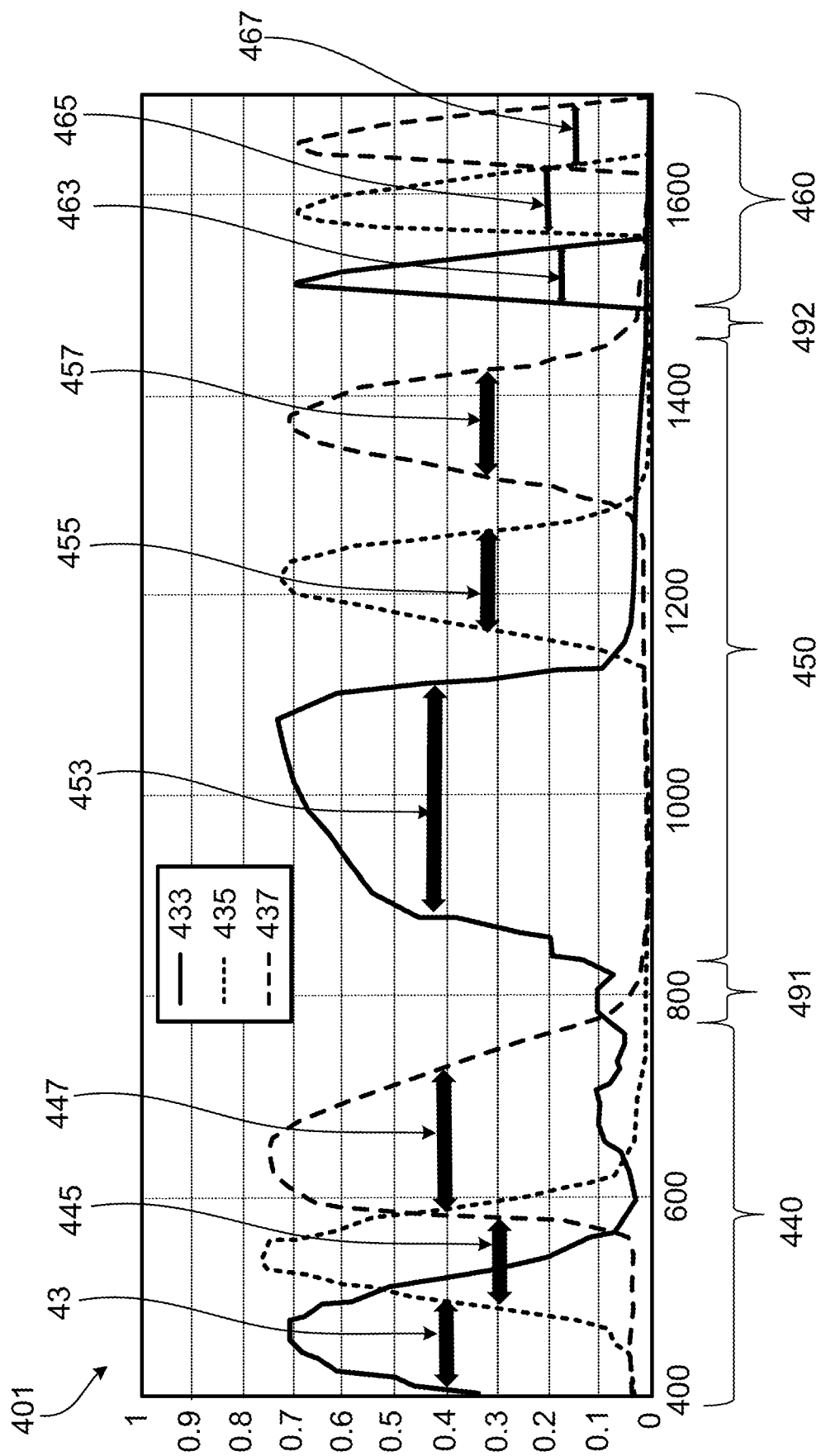
FIG. 4D shows the spectral response of an example image sensing apparatus, in accordance with technology described herein.

FIG. 4D shows a spectral response of a filter according to aspects of the present disclosure. While the graph 301 of the spectral response 333, 335, 337 of the image sensing apparatus 300 of FIG. 3A illustrates a filter array 310 having two wavelength ranges, the filter array 310 may define three or more wavelength ranges, depending on the number and frequency range of the individual pass bands of the filters 313a, 313b, 313c, 313d. The present graph 401 of FIG. 4D shows the spectral response 433, 435, 437 of a filter array 310 with three wavelength ranges 440, 450, 460. FIG. 4D shows each spectral response 433, 435, 437 having a tri-modal shape, with each spectral response 433, 435, 437 defines a passband in each of the three wavelength ranges 440, 450, 460. For example, a first spectral response 433 (e.g., of a first filter 313) forms a first passband 443 in a first wavelength range 440, a second passband 453 in a second wavelength range 450, and a third passband 463 in a third wavelength range 460. A second spectral response 435 (e.g., of a second filter 313b, 313c) forms a first passband 445 in a first wavelength range 440, a second passband 455 in a second wavelength range 450, and a third passband 467 in a third wavelength range 460, and a third spectral response 437 (e.g., of a third filter 313d) forms a first passband 447 in a first wavelength range 440, a second passband 457 in a second wavelength range 450, and a third passband 467 in a third wavelength range 460. In addition, the passbands 443, 445, 447 of the first wavelength range 440 are distinct from the passbands 453, 455, 457 of the second wavelength range 450, thereby forming a first overlapping stopband 491 therebetween. Similarly, the passbands 453, 455, 457 of the second wavelength range 450 are distinct from the passbands 463, 465, 467 of the third wavelength range 460, thereby forming a second overlapping stopband 492 therebetween. In this configuration, a filter array 310 having the spectral response of FIG. 4D can generate representations of at least three distinct images of the same surgical scene by first illuminating the surgical scene with an illumination range corresponding to the first wavelength range 440 to generate a first image, then illuminating the surgical scene with an illumination range corresponding to the second wavelength range 450 to generate a second image, and finally illuminating the surgical scene with an illumination range corresponding to the third wavelength range 460 to generate a third image.

Figure 5B:
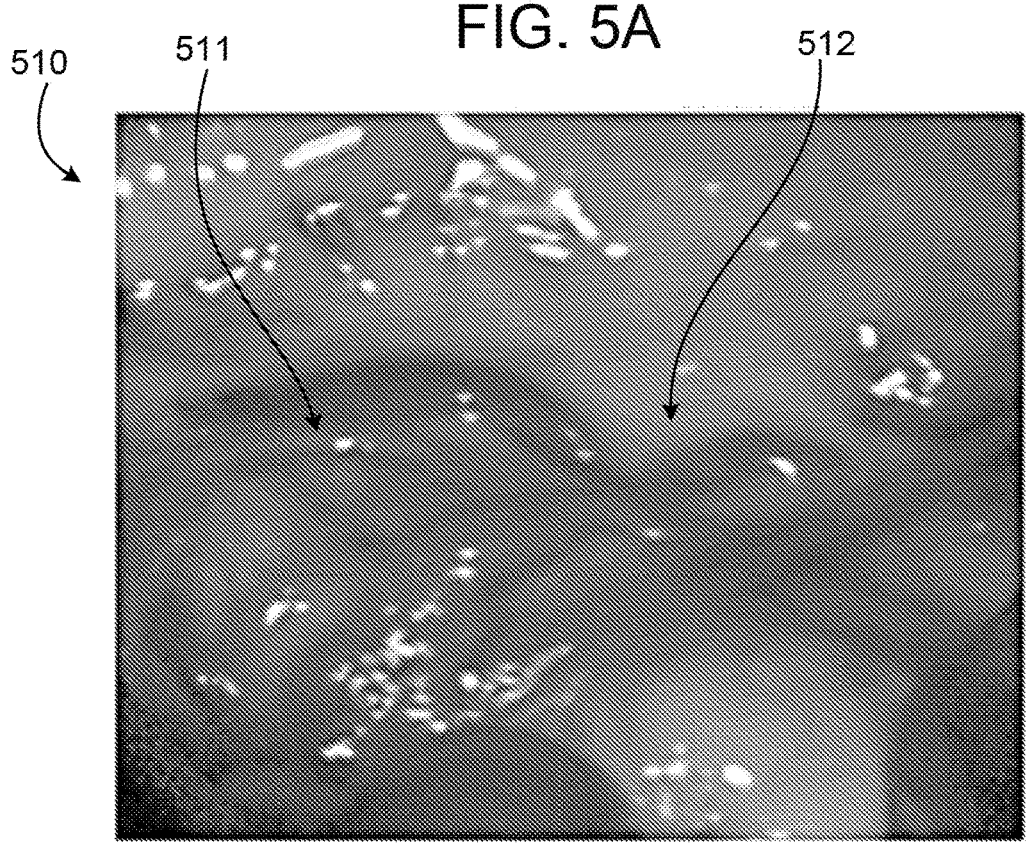
FIG. 5B shows the same portion of the human body, as in FIG. 5A, captured in a second image obtained using illumination in a second illumination range, in accordance with technology described herein.

The technology described herein can allow for selecting imaging wavelengths in the near-infrared (NIR) or infrared (IR) spectrum, such that the visible differences between different tissues (collagen and fat, in one example) can be enhanced in the presented images. In some implementations, this can be achieved by selecting particular wavelengths (or ranges of wavelengths) in the NIR and/or IR range (e.g., in the range of 850-2000 nm) in accordance with the tissues that are being imaged, and capturing images based on such wavelengths. For example, and as shown in FIGS. 5A and 5B, in order to enhance visible differences between collagen and lipid, tissues can be imaged using a first wavelength range, which includes the visible wavelengths to create a true-color image of the tissues (e.g., FIG. 5A), and then imaged a second time using a second wavelength range, in which the absorption of electromagnetic radiation by different passbands of the filter array 310 enables color-differential of the collagen and fat (e.g., FIG. 5B).

In one example, the absorption of electromagnetic radiation by one passband of the filter in the second wavelength range is significantly higher than that by the lipid (or, correspondingly, the amount of electromagnetic radiation reflected from or transmitted through collagen is lower than the corresponding amount for lipid), and in another passband band of the filter array 310 in the second wavelength range, the ratio of absorption by the lipid compared to collagen is significantly different (or, correspondingly, the ratio of electromagnetic radiation reflected from or transmitted through lipid compared to collagen is different), then the resulting second image will represent the collagen and fat in distinct false-colors. In some implementations, such complementary absorption characteristics can cause the corresponding wavelengths to be absorbed by the tissues substantially differently, thereby enhancing the visible differences in the resulting image.

In some implementations, the particular wavelengths or wavelength ranges for imaging the different tissues can be selected based on experimental data. For example, referring to the plots 205 and 210 in FIG. 2, the absorption for lipid at around 1200 nm is seen to be significantly higher than that for collagen. In addition, the absorption for collagen at around 1350 nm is seen to be significantly higher than that for lipid. Therefore, passbands of 1200-1250 nm and 1300-1350 nm can be selected in the second wavelength range for enhancing the visible differences between a ureter and the adjacent fat layers. FIG. 5A shows a true-color image of a surgical scene, captured by the image sensing apparatus 300 when illuminated by electromagnetic radiation in visible wavelength-illumination range, where the ureter 501 and the surrounding tissue are visible, but not easily identifiable due to their similar absorption coefficients (as shown in FIG. 2 in the visible spectrum). FIG. 5B shows the same portion of the human body, as in FIG. 5A, captured using image sensing apparatus 300 when illuminated by a second wavelength illumination range that includes the 1200-1250 nm and 1300-1350 nm wavelength ranges where, and a first passband includes the 1200-1250 nm range, and a second passband includes the 1300-1350 range.

In some implementation, instead of wavelength ranges, one or more discrete wavelengths may also be selected for imaging particular tissues. For example, 1200 nm and 1350 nm wavelengths may be selected to enhance visible difference between collagens and lipids in the resultant image. As seen from FIG. 5B, due to the different absorption characteristics of collagen and fat for the selected wavelengths, the image may be presented to accentuate visibly the differences between the representation of the ureter 511 and the representation of the fat layers 512 in FIG. 5B are significantly enhanced in the visible image presented as compared to the differences between the corresponding portions 501 and 502, respectively, in FIG. 5A. Subsequently, a combination image (not shown) can be generated by combining the first and second images (e.g., FIGS. 5A and 5B) into a representation that shows the true-color details, along with highlighting of color features visible in second image (e.g., by making the ureter neon blue or some other vibrant color in the combined image).

In some implementations, one or more additional wavelengths or wavelength ranges may also be selected for the imaging the different tissues. The additional wavelengths may be selected based on various criteria. In some implementations, a third wavelength or wavelength range may be selected to improve the overall image presented by using the third wavelength to estimate one or more characteristics of the surgical site. For example, the third wavelength or wavelength range can be selected such that the absorption or reflectance/transmission characteristics for that wavelength or wavelength range are substantially similar for the tissues being imaged. In that case, the reflectance associated with the third wavelength or wavelength range provides a local reference brightness that visibly enhances the differences between the tissues of interest. In some cases, this can be important from a human perception perspective, and potentially improve intelligibility of the rendered images for surgeons.

In some implementations, the third wavelength or wavelength range may also be selected to further improve the differentiability between the tissues. For example, in the case of imaging collagen and lipid, the third wavelength or wavelength range can be selected such that at the selected wavelength or wavelength range, the absorption of electromagnetic radiation by the collagen is significantly higher than that by the lipid, or correspondingly, the amount of electromagnetic radiation reflected from or transmitted through collagen is lower than the corresponding amount for lipid. A wavelength or wavelength range with the reverse characteristics may also be chosen. For example, the third wavelength or wavelength range can be selected such that at the selected wavelength or wavelength range, the absorption of electromagnetic radiation by the lipid is significantly higher than that by the collagen, or correspondingly, the amount of electromagnetic radiation reflected from or transmitted through lipid is lower than the corresponding amount for collagen.

In some implementations, the second and third wavelength ranges are outside the visible range of wavelengths. In some implementations, the entirety of the first wavelength range lies inside the visible spectrum. In some implementations, a portion of the first wavelength range lies outside the visible spectrum. In some implementations, a portion of the second wavelength range lies within the visible spectrum. In some implementations, the third wavelength range is inside the visible range of wavelengths such that a combination of wavelengths in the visible and IR/NIR range is used for the overall imaging process.

Figure 6:
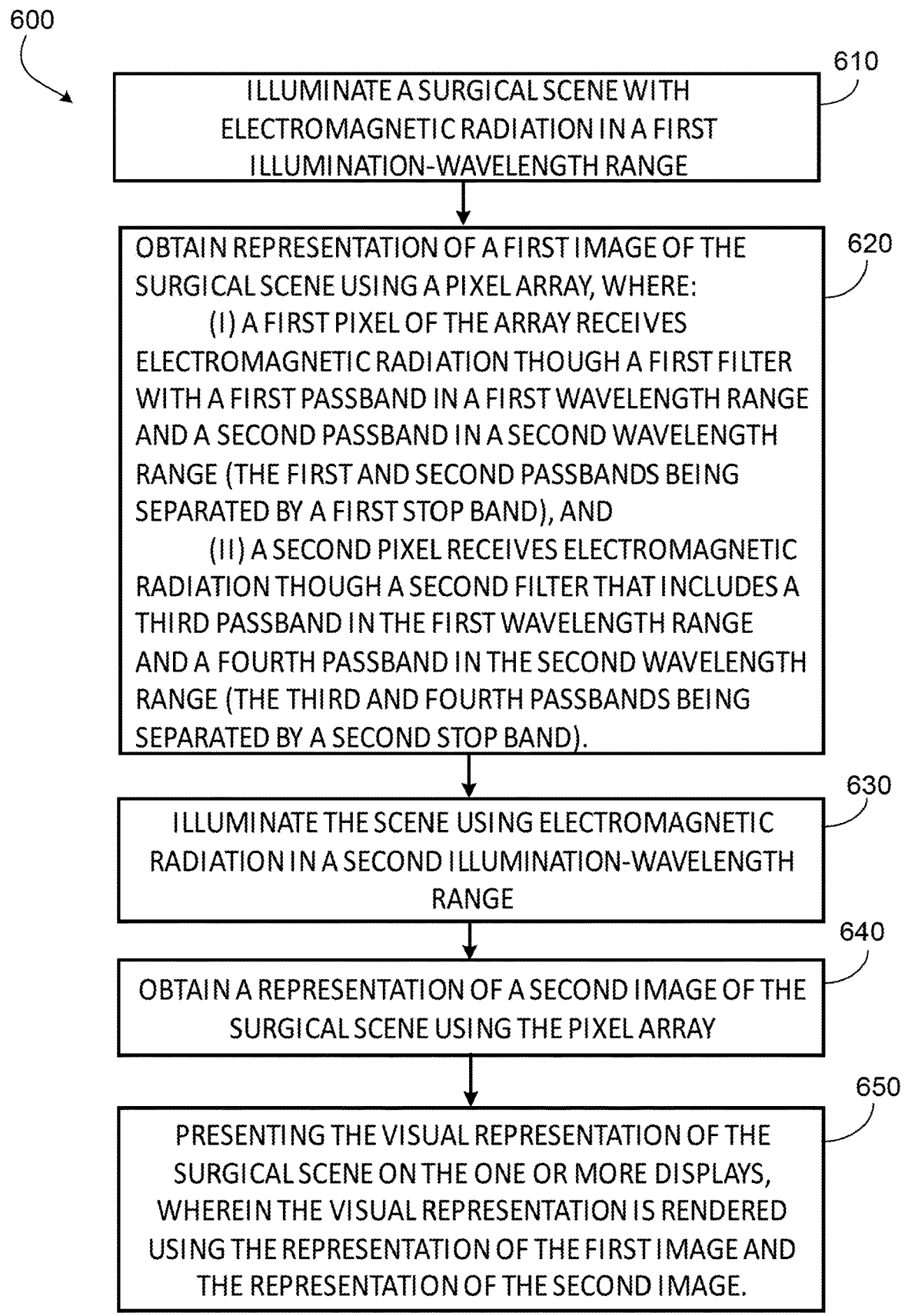
FIG. 6 is a flowchart illustrating an example process of providing visual feedback during a surgical process.

FIG. 6 is a flowchart illustrating an example process 600 of providing visual feedback during a surgical process using a visual representation of a surgical scene rendered on a display associated with a surgical device. In some implementations, at least a portion of the process 600 may be executed at a surgeon's console of a computer-assisted tele-operated surgery system (e.g., by the processing device 43 of the surgeon's console 40 depicted in FIG. 2). Operations of the process 600 include obtaining a representation of a first image of the surgical scene with an image sensing apparatus using electromagnetic radiation of a first wavelength range that lies inside the visible range of wavelengths by first illuminating the surgical scene with electromagnetic radiation in a first illumination-wavelength range (610). The first illumination-wavelength range (which in some cases may include one or more discrete wavelengths) can be selected such that an amount of electromagnetic radiation received from the surgical scene lies within a first wavelength range of an image sensing apparatus according to aspects disclosed herein. Next, based on the first illuminating, the image sensing apparatus obtains a representation of the first image using a pixel array that includes a filter array that has individual filters each forming a distinct passband in each of the first wavelength range and a second wavelength range (620). In some instances, the first image primarily corresponds to electromagnetic radiation filtered by the passbands of the first wavelength range of the filter. Next, the surgical scene is illuminated using electromagnetic radiation in a second illumination-wavelength range (630). The second illumination-wavelength range (which in some cases may include one or more discrete wavelengths) can be selected such that an amount of electromagnetic radiation received from the surgical scene corresponds to a second wavelength range of the image sensing apparatus according to aspects disclosed herein. Next, based on the second illuminating, the image sensing apparatus obtains a representation of the second image using the pixel array (640). In some instances, the second image primarily corresponds to electromagnetic radiation filtered by the passbands of the second wavelength range of the filter. Finally, the process including presenting the visual representation of the surgical scene on the one or more displays, wherein the visual representation is rendered using the representation of the first image and the representation of the second image (650). In some instances, the visual representation includes a single image formed using a combination of all or a select portion of the first and second images In some implementations, the wavelength range of the passbands of the filter array can be selected to corresponds to the absorption or reflectance properties of different tissues types, such as lipid, or muscle, such that that passbands enable images to be obtained with different color information corresponding to the different tissues types in order to enhance the visibility of the selected tissues. For example, a first passband can be sensitivity to collagen and not lipid, and a second passband can be sensitive to lipid and not collages, which allows for enhancing visible differences between a ureter and surrounding fat layers in an image of a corresponding surgical site, as rendered on a surgeon's console.

In some implementations, the process 600 also includes obtaining a representation of a second image of the surgical scene using electromagnetic radiation received with a filter array with passbands in a second wavelength range that lies outside the visible range of wavelengths (620) The passbands in the second wavelength range can be selected such that an amount of electromagnetic radiation of in second wavelength range received from the second tissue type through one passbands is substantially different than an amount of electromagnetic radiation of the second wavelength range received through a different passband from the first tissue type. In some implementations, each of the first wavelength range and the second wavelength range are in the range 700-2000 nm. In some implementations, the visible spectrum lies within the first wavelength range, and at least a portion of the second wavelength range lies outside of the visible spectrum, such that the passbands in the first wavelength range can obtain a true-color representation of the surgical scene in the visible spectrum when the surgical scene is illuminated with a first illumination-wavelength range (e.g., a visible light source), and the passbands in the second wavelength range obtain a representation of the surgical scene outside the visible spectrum when the surgical scene is illumination with a second illumination-wavelength range (e.g., an infrared or near-infrared light source). In some implementations, the specific passbands in the second wavelength range are selected to enhance the visual distinction between different tissues types. For example, a wavelength range of a first passband in the second wavelength range can be in the range 1300-1350 nm and the wavelength range of a second passband in the second wavelength range can be in the range 1200-1250 nm.

In some implementations, obtaining the representation of the first or second image of the surgical scene can include illuminating the surgical scene using electromagnetic radiation of the first wavelength or the second wavelength, and generating the representation of the first image or second image, respectively, using data captured by an image sensing apparatus configured to sense portions of the electromagnetic radiation reflected or transmitted from the surgical scene. In some implementations, the illumination wavelengths can be selected such that portions of the illumination reflected or transmitted from the target tissues are in the corresponding selected wavelength ranges. In some implementations, illuminating the surgical scene using electromagnetic radiation can include illuminating the surgical scene using electromagnetic radiation of the first wavelength during a first time period, and illuminating the surgical scene using electromagnetic radiation of the second wavelength during a second time period. The second time period can be completely, or at least partially non-overlapping with the first time period.

In some implementations, a representation of a third image of the surgical scene can be obtained based on a distinct set of passbands in a third wavelength range of the filter array when the surgical scene is illuminated in a third illumination-wavelength range that corresponds to the third wavelength range of the filter array (where the third illumination-wavelength range may include one or more discrete wavelengths). In some instances, one or both of the third wavelength range of the filter array and the third illumination-wavelength range lies outside the visible range of wavelengths. In some implementations, the process include presenting a visual representation of the surgical scene on the display, where the visual representation includes the third image. The visual representation presented on the surgeon's console can be rendered also using a combination visual representation using all or a portion of the first, second, and third images. Similar to the second wavelength range, the third illumination-wavelength range or the third wavelength range of the filter array may be selected based on various criteria. For example, to improve the overall reflectance in the resulting image, to further improve the differentiability between the tissues, and/or improve human-perceptibility of the final rendered image. In some implementations, the third wavelength range can be selected based on interaction of the different target tissues with electromagnetic radiation in the third wavelength range. For example, an absorption of electromagnetic radiation in the third wavelength range for one tissue type (e.g., lipid) can be substantially equal to (or significantly different from) an absorption of electromagnetic radiation in the third wavelength range for a different tissue type (e.g., collagen).

Operations of the process 600 can also include presenting the visual representation of the surgical scene on the display, wherein the visual representation is rendered using the representation of the first image and the representation of the second image (620). In some implementations, the representations of the first and second images may be processed in various ways to improve intelligibility and/or presentation of the visual representation (650). For example, the representations of the first and/or second images may be mapped on to other portions of the spectrum (e.g., within the visible range of the spectrum) to adjust the appearance of the visual representation. This may be done, for example, to influence the colors in which the different tissues are represented. In one particular example, by mapping a 1300-1350 nm range to the "green" portion of the visible spectrum, a 1200-1250 nm range to the "blue" portion of the visible spectrum, and selecting a third wavelength range in the "red" portion of the visible spectrum, the color of fat in the visual representation can be made to appear natural (or at least close to natural), and blood vessels can be made to appear blue. In some cases, the color mappings may be made in accordance with typical assumptions made by the surgeons about tissue types, and/or to improve surgeons' understanding of the visual representation. In some implementations, other forms of presentations may be used. For example, a small inset color image can be presented in a picture-in-picture configuration, the color image corresponding to the first or second images, or an image generated using some combination of information from the first and second images.

In some implementations, the first image is a visible light image obtained using a first illumination-wavelength range that is substantially white light illumination to present a true-color visual representation of the surgical scene on the display, and the second image is an infrared image obtained using a second illumination-wavelength range that is substantially near infrared or infrared illumination to present an infrared representation of the surgical scene on the display. The infrared image can be used to modify the white light image to increase the visual saliency of particular tissue features. In some implementations, the capture of and use of the second image can be made using only one or a few narrow wavelengths of infrared light, such that only one of the passbands in the second wavelength range are represented in the second image (e.g., a monochrome image). In some instances, the white light image presents an image with particular features that are discriminated by the second wavelength ranges.

Other variations of the process described above are also possible. For example, the first and second wavelength ranges can both lie outside the visible spectrum, and the representation of the first image (corresponding to the first wavelength range) and the representation of the second image (corresponding to the second wavelength range) can be used in conjunction with a separately captured visible light image (obtained using a separate sensor under substantially white light illumination) to present the visual representation of the surgical scene on the display. The first and second images, individually or in combination, can be used to modify the white light image to increase the visual saliency of particular tissue features. In some implementations, the capture of and use of the second image can be made optional, and only the first image may be used in conjunction with the visible light image in generating the visual representation. The white light image presents an image with particular features that are discriminated by the first and (optionally) second wavelength ranges.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media or storage device, for execution by, or to control the operation of, one or more data processing apparatus, e.g., a programmable processor, a DSP, a microcontroller, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed one or more processing devices at one site or distributed across multiple sites and interconnected by a network.

Actions associated with implementing all or part of the functions can be performed by one or more programmable processors or processing devices executing one or more computer programs to perform the functions of the processes described herein. All or part of the functions can be implemented as, special purpose logic circuitry, e.g., an FPGA and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Particular embodiments of the subject matter have been described. Other embodiments are within the scope of the following claims.

What is claimed is:

1. An image sensing apparatus comprising:
a pixel array comprising two or more photo-sensor elements;
a first optical filter disposed on a first photo-sensor element of the pixel array, the first optical filter configured such that a spectral response of the first optical filter includes:

a first passband in a first wavelength range, and
a second passband in a second wavelength range, the first passband and the second passband being separated by a first stop band, the second passband having a wavelength between 1200 and 1250 nm; and
a second optical filter disposed on a second photo-sensor element of the pixel array, the second optical filter configured such that a spectral response of the second optical filter includes:
a third passband in the first wavelength range, and
a fourth passband in the second wavelength range, the third passband and the fourth passband being separated by a second stop band, the fourth passband having a wavelength between 1300 and 1350 nm;
wherein the first and second optical filters are arranged in a Bayer pattern, the first wavelength range is non-overlapping with second wavelength range, and the second optical filter is configured such that absorption characteristic of a first tissue type in the third passband is higher than absorption characteristic of a second tissue type in the third passband, and absorption characteristic of the second tissue type in the fourth passband is higher than absorption characteristic of the first tissue type in the fourth passband.

2. The image sensing apparatus of claim 1, comprising a third optical filter disposed on a third photo-sensor element of the pixel array, the third optical filter configured such that a spectral response of the third optical filter includes:
a fifth passband in the first wavelength range, and
a sixth passband in the second wavelength range, the fifth passband and the sixth passband being separated by a third stop band.

3. The image sensing apparatus of claim 2, wherein a portion of the first stop band overlaps with a portion of the second stop band and a portion of the third stop band.

4. The image sensing apparatus of claim 1, comprising one or more processing devices configured to generate a representation of an image of using output signals from the pixel array; and
circuitry configured to provide the output signals from the pixel array to the one or more processing devices.

5. The image sensing apparatus of claim 4, wherein the one or more processing devices are configured to generate the representation of the image by combining electromagnetic radiation received by the pixel array in the first wavelength range, and electromagnetic radiation received by the pixel array in the second wavelength range.

6. The image sensing apparatus of claim 5, wherein the one or more processing devices are configured to:
present the representation of the image on one or more displays.

7. The image sensing apparatus of claim 1, wherein a portion of the first stop band overlaps with a portion of the second stop band.

8. The image sensing apparatus of claim 1, wherein the first wavelength range is within the visible wavelength range, and wherein the second wavelength range is outside the visible wavelength range.

9. The image sensing apparatus of claim 1, wherein the first and second wavelength ranges are in the range 400-2000 nm.

10. A surgical system comprising:
one or more display devices;
an image sensing apparatus configured to receive electromagnetic radiation reflected or transmitted from a surgical scene, the image sensing apparatus comprising:
a pixel array comprising two or more photo-sensor elements, and
a first optical filter disposed on a first photo-sensor element of the pixel array, the first optical filter configured such that a spectral response of the first optical filter includes:
a first passband in a first wavelength range, and
a second passband in a second wavelength range, the first passband and the second passband being separated by a first stop band, the second passband having a wavelength between 1200 and 1250 nm, and
a second optical filter disposed on a second photo-sensor element of the pixel array, the second optical filter configured such that a spectral response of the second optical filter includes:
a third passband in the first wavelength range, and
a fourth passband in the second wavelength range, the third passband and the fourth passband being separated by a second stop band, the fourth passband having a wavelength between 1300 and 1350 nm;
wherein the first and second optical filters are arranged in a Bayer pattern, the first wavelength range is non-overlapping with second wavelength range, and the second optical filter is configured such that absorption characteristic of a first tissue type in the third passband is higher than absorption characteristic of a second tissue type in the third passband, and absorption characteristic of the second tissue type in the fourth passband is higher than absorption characteristic of the first tissue type in the fourth passband;
one or more processing devices configured to:
obtain a representation of a first image of a surgical scene using electromagnetic radiation in the first wavelength range,
obtain a representation of a second image of the surgical scene using electromagnetic radiation in the second wavelength range, and
present a visual representation of the surgical scene on the one or more displays, wherein the visual representation is rendered using the representation of the first image and the representation of the second image; and
an input device configured to receive a user-input for controlling at least a portion of a surgical device.

11. The system of claim 10, wherein obtaining the representation of the first and second image, comprises:
illuminating the surgical scene using electromagnetic radiation in a first illumination range and a second illumination range; and
obtaining the representations of the first image or second image responsive to illuminating the surgical scene using electromagnetic radiation in the first illumination range and second illumination range, respectively.

12. The system of claim 11, wherein illuminating the surgical scene using electromagnetic radiation in the first wavelength range or the second wavelength range comprises:
illuminating the surgical scene using electromagnetic radiation in the first illumination range during a first time period; and
illuminating the surgical scene using electromagnetic radiation in the second illumination range during a second time period that is at least partially non-overlapping with the first time period.

13. The system of claim 10, wherein the representation of the second image is obtained at substantially the same time as the representation of the first image.

14. A method of providing visual feedback during a surgical process using a visual representation of a surgical scene rendered on one or more displays associated with a surgical device, the method comprising:
  illuminating a surgical scene using electromagnetic radiation in a first illumination-wavelength range;
  obtaining, responsive to illuminating the surgical scene using electromagnetic radiation in the first illumination-wavelength range, a representation of a first image of the surgical scene using a pixel array including two or more photo-sensor elements, wherein a first photo-sensor element of the two or more photo-sensor elements is configured to receive electromagnetic radiation though a first filter that includes a first passband in a first wavelength range and a second passband in a second wavelength range, the second passband having a wavelength between 1200 and 1250 nm, the first passband and the second passband being separated by a first stop band, and wherein a second photo-sensor element of the two or more photo-sensor elements is configured to receive electromagnetic radiation though a second filter that includes a third passband in the first wavelength range and a fourth passband in the second wavelength range, the fourth passband having a wavelength between 1300 and 1350 nm, the third passband and the fourth passband being separated by a second stop band wherein the first and second optical filters are arranged in a Bayer pattern, the first wavelength range is non-overlapping with second wavelength range, and the second optical filter is configured such that absorption characteristic of a first tissue type in the third passband is higher than absorption characteristic of a second tissue type in the third passband, and absorption characteristic of the second tissue type in the fourth passband is higher than absorption characteristic of the first tissue type in the fourth passband;
  illuminating the surgical scene using electromagnetic radiation in a second illumination-wavelength range;
  obtaining, responsive to illuminating the surgical scene using electromagnetic radiation in the second illumination-wavelength range, a representation of a second image of the surgical scene using the pixel array; and
  presenting the visual representation of the surgical scene on the one or more displays, wherein the visual representation is rendered using the representation of the first image and the representation of the second image.

15. The method of claim 14, wherein the first image corresponds to the electromagnetic radiation received through the first and third passbands and the second image corresponds to the electromagnetic radiation received through the second and fourth passbands.

16. The method of claim 15, wherein illuminating the surgical scene using electromagnetic radiation in the first illumination-wavelength range comprises illuminating the surgical scene during a first time period; and wherein illuminating the surgical scene using electromagnetic radiation in the second illumination-wavelength range comprises illuminating the surgical scene during a second time period that is at least partially non-overlapping with the first time period.

17. The method of claim 14, wherein the first wavelength range of the first and third passbands lies inside the visible range, and wherein the second wavelength of the second and fourth passbands range lies outside the visible range.

18. The method of claim 14, wherein the electromagnetic radiation in the first illumination-wavelength range lies inside the visible range, and wherein electromagnetic radiation in second illumination-wavelength range lies outside the visible range.

19. The method of claim 14, further comprising:
  illuminating the surgical scene using electromagnetic radiation in a third illumination-wavelength range;
  obtaining, responsive to illuminating the surgical scene using electromagnetic radiation in the third illumination-wavelength range, a representation of a third image of the surgical scene using the pixel array,
  wherein the first photo-sensor element is configured to receive electromagnetic radiation through the first filter that includes a fifth passband in a third wavelength range and, wherein the second photo-sensor element is configured to receive electromagnetic radiation through the second filter that includes a sixth passband in the third wavelength range, wherein the first and second filters together define a third stop band separating the fifth and sixth passbands from the first, second, third, and fourth passbands; and
  presenting the visual representation of the surgical scene on the display, wherein the visual representation is rendered also using the representation of the third image.

20. The method of claim 19, wherein the first tissue type is collagen and the second tissue type is lipid.

* * * * *

UNITED STATES PATENT AND TRADEMARK OFFICE
CERTIFICATE OF CORRECTION

PATENT NO. : 12,108,170 B2
APPLICATION NO. : 17/259834
DATED : October 1, 2024
INVENTOR(S) : William Jason Culman et al.

Page 1 of 1

It is certified that error appears in the above-identified patent and that said Letters Patent is hereby corrected as shown below:

On the Title Page

Add item (60):
-- (60) Provisional application No. 62/697,102, filed on Jul. 12, 2018. --

Signed and Sealed this
Fourth Day of March, 2025

Coke Morgan Stewart
*Acting Director of the United States Patent and Trademark Office*